United States Patent [19]

Yamada et al.

[11] Patent Number: 4,661,457
[45] Date of Patent: Apr. 28, 1987

[54] METHOD FOR CULTIVATION OF PSEUDOMONAS BACTERIA

[75] Inventors: Hideaki Yamada, 19-1, Matsugasaki-Kinomoto-Cho, Sakyo-Ku, Kyoto-Shi, Kyoto-Fu; Kanehiko Enomoto, Yokohama; Ichiro Watanabe, Yokosuka, all of Japan

[73] Assignees: Nitto Kagaka Kogyo Kabushiki Kaisha, Tokyo; Hideaki Yamada, Kyoto, both of Japan

[21] Appl. No.: 569,047

[22] Filed: Jan. 9, 1984

[30] Foreign Application Priority Data

Jan. 10, 1983 [JP] Japan ................................. 58-1997

[51] Int. Cl.$^4$ ................ C12N 1/38; C12N 1/20; C12N 9/78; C12R 1/38
[52] U.S. Cl. ................................... 435/244; 435/227; 435/253; 435/874
[58] Field of Search ............... 435/227, 244, 874, 280, 435/253

[56] References Cited

U.S. PATENT DOCUMENTS

| | | | |
|---|---|---|---|
| 3,989,592 | 11/1976 | Leavitt | 435/874 |
| 4,001,081 | 1/1977 | Commeyras et al. | 435/832 |
| 4,366,250 | 12/1982 | Jallageas et al. | 435/280 |
| 4,390,631 | 6/1983 | Watanabe et al. | 435/129 |
| 4,440,858 | 4/1984 | Yamaguchi et al. | 435/129 |

FOREIGN PATENT DOCUMENTS 58-01784 5/1983 Japan ................................. 435/129

OTHER PUBLICATIONS

Manual of Clinical Microbiology, 2nd ed. (1974), American Society for Microbiology, Washington, D.C., p. 896.
Asano et al, Agricultural Biological Chemistry, (1982), vol. 46, pp. 1165–1174.
Asano et al, Agricultural Biological Chemistry (1982), vol. 46, pp. 1175–1181.
Agricultural and Biological Chemistry (1976), vol. 40, No. 8, pp. 1515–1522.
Journal of Fermentation Technology (1974), vol. 52, p. 567.
Journal of Fermentation Technology (1972), vol. 50, p. 637.
Laboratory Methods in Microbiology (1966), pp. 38–41.
Journal of General and Applied Microbiology (1982), vol. 28, pp. 359–368.

*Primary Examiner*—Sidney Marantz
*Assistant Examiner*—William J. Herald
*Attorney, Agent, or Firm*—Robert E. Burns; Emmanuel J. Lobato; Bruce L. Adams

[57] ABSTRACT

Cells of Pseudomonas bacteria having a high nitrile hydratase activity can be obtained in a high yield by adding to a culture medium cysteine and (or) cystine in the preparation of cells of bacteria having nitrile hydratase activity by cultivating under nitrile hydratase-inducing conditions Pseudomonas bacteria capable of producing nitrile hydratase.

5 Claims, No Drawings

METHOD FOR CULTIVATION OF PSEUDOMONAS BACTERIA

BACKGROUND OF THE INVENTION

The present invention relates to a method of producing in a high yield cells of Pseudomona bacteria having a high nitrile hydratase activity.

In recent years, the technology of immobilized enzymes or microorganisms has developed rapidly, resulting in increasing attempts to utilize microorganisms and enzymes as they are or in an immobilized state as catalysts for various single or complex chemical reactions.

Nitrile hydratase has been found by Hideaki Yamada, one of the present inventors, et al. as an enzyme capable of hydrating nitriles to produce the corresponding amides. (Reference: Agric. Biol. Chem. 46 1165 (1982)) As one example of the utilization of this enzyme, a method for preparation of acrylamide from acrylonitrile in the presence of bacteria having nitrile hydratase has been proposed. (References: Japanese Patent Laid-Open Pub. No. 86093/1983 (Japanese Patent Appln. No. 184688/1981) and Agric. Biol. Chem. 46 1183 (1982))

Under these circumstances, a method that can ensure the production of cells of Pseudomonas bacteria having a high nitrile hydratase activity in a high yield would be remarkably beneficial.

SUMMARY OF THE INVENTION

An object of the present invention is to provide a method for production of cells of Pseudomonas bacteria having a high nitrile hydratase activity in a high yield by adding to a culture medium a specific substance i.e., cysteine and (or) cystine in the cultivation of such bacteria.

Thus, a distinguishing feature of the method for cultivation of Pseudomonas bacteria having a high nitrile hydratase activity according to this invention is the addition of cysteine and (or) cystine to a culture medium in the preparation of cells of bacteria having nitrile hydratase activity by cultivating under nitrile hydratase-inducing conditions Pseudomonas bacteria capable of producing nitrile hydratase.

We have found that, by adding cysteine and (or) cystine to the culture medium during the cultivation of Pseudomonas bacteria, the nitrile hydratase activity per unit culture fluid increases remarkably. More specifically, for example, the addition of cysteine or cystin can increase the nitrile hydratase activity per unit culture fluid to a level nearly three times that obtained when the cysteine or cystine is not added.

This increase in nitrile hydratase activity per unit culture fluid is presumably traceable to the increase in cell concentration (i.e., yield) and cell activity (i.e., quantity of the nitrile hydratase in the cells).

DETAILED DESCRIPTION OF THE INVENTION

Pseudomonas Bacteria

The bacteria used in the present invention are Pseudomonas bacteria having nitrile hydratase activity and the capability of hydrating nitriles, particularly acrylonitrile, to produce the corresponding amides, particularly acrylamide. Specific examples of such bacteria are *Pseudomonas chlororaphis*, strain B 23 (FERM BP-187), and Pseudomonas sp., strain PS 1 (FERM BP-188), disclosed in Japanese Patent Laid-Open Pub. No. 86093/1983 mentioned above. The principal microbiological properties of these bacteria are as follows.

TABLE 1

| | | B 23 | PS 1 |
|---|---|---|---|
| (a) | Morphology | | |
| 1 | Shape and size of cell | bacillus 0.8–1.1 × 1.6–2.7 μm | bacillus 0.8–1.1 × 1.3–1.9 μm |
| 2 | Polymorphism | none | none |
| 3 | Motility | motile one to three polar flagella | motile with polar flagella |
| 4 | Formation of spores | none | none |
| 5 | Gram staining | − | − |
| 6 | Acid-fast property | − | − |
| (b) | Growth on various culture media | | |
| 1 | Bouillon-agar plate culture | spherical, convex, glossy, translucent and yellow | smooth, homogeneous, glossy, and mucoidal |
| 2 | Bouillon-agar slant culture | small colony formed | smooth, glossy, translucent, and yellow |
| 3 | Bouillon liquid culture | precipitated | |
| 4 | Bouillon-gelatin stab culture | liquefied (+) | − |
| 5 | Litmus-milk | acidic: peptonized, not coagulated | alkaline: peptonized, not coagulated |
| (c) | Physiological properties | | |
| 1 | Reduction of nitrate | + | − |
| 2 | Denitrification | + | − |
| 3 | MR test | − | − |
| 4 | VP test | − | − |
| 5 | Formation of indole | − | − |
| 6 | Formation of hydrogen sulfide | − | − |
| 7 | Hydrolysis of starch | − | − |
| 8 | Utilization of citric acid | Simon's culture: + | Simon's culture: + |
| 9 | Utilization of inorganic nitrogen source | ammonium salt: + | ammonium salt: + |
| 10 | Formation of pigments | King-A culture: − King-B culture: + green (water-soluble) | King-A culture: − King-B culture: + green (water-soluble) |
| 11 | Urease | − | − |
| 12 | Oxidase | + | + |
| 13 | Catalase | + | + |
| 14 | Growth range | pH: 6.0–9.9 temperature: 5–36.5° C. | |
| 15 | Behavior toward oxygen | aerobic | aerobic |
| 16 | O-F Test | oxidized | oxidized |
| 17 | Formation of acid & gas from saccharide | Formation of acid / Formation of gas | Formation of acid / Formation of gas |
| | D-glucose | + / − | + / − |
| | D-mannose | + / − | + / − |
| | D-fructose | − / − | − / − |
| | D-galactose | + / − | + / − |
| | maltose | − / − | − / − |
| | sucrose | − / − | − / − |
| | lactose | − / − | − / − |
| | trehalose | − / − | − / − |

TABLE 1-continued

|  |  |  |  |  |  |
|---|---|---|---|---|---|
|  | D-mannitol | — | — | — | — |
|  | glycerol | — | — | — | — |
|  | starch | — | — | — | — |
| 18 | Nutritive requirements | none |  | none |  |
| 19 | Other properties | See remarks |  |  |  |

Remarks:
Aminopeptidase +
Formation of levan +
from saccharose
Formation of poly- —
β-hydroxybutyrate
GC content 64.6%

Enzymatic Activity Improving Agent

In the present invention, cysteine and (or) cystine are (is) used as enzymatic activity improving agents. These enzymatic activity improving agents can be used singly or in the form of a mixture.

The cysteine used in the present invention may be D-cysteine, L-cysteine or D,L-cysteine while the cystine may be D-cystine, L-cystine or D,L-cystine, and these enzymatic activity improving agents can be used singly or in the form of a mixture of two or more members as has been set forth above.

Cultivation-Practice of the Present Invention

A preferred embodiment of this invention will be described below.

At least one enzymatic activity improving agent selected from D-cysteine, L-cysteine, D,L-cysteine, D-cystine, L-cystine, and D,L-cystine is added at one time or sequentially to a culture medium containing: carbon sources such as glucose, fructose, sucrose, dextrins, glycerol, ethanol, and succinic acid; nitrogen sources such as ammonia, ammonium sulfate, ammonium chloride, ammonium nitrate, and urea; organic nutriment sources such as yeast extract, meat extract, malt extract, casein hydrolyzate, and peptone; inorganic salts such as phosphates; magnesium, potassium, and iron and like metals in trace amounts; and other substances at a concentration of 0.1 to 5.0 g/liter, preferably 0.5 to 2.0 g/liter. The term "sequentially" as used herein is intended to mean both "continuously" and "intermittently".

This culture medium is inoculated with Pseudomonas bacteria having nitrile hydratase activity, and cultivation is carried out under aerobic conditions while an enzyme inducing agent is added to induce nitrile hydratase. Examples of the enzyme inducing agent are propionitrile, isobutyronitrile, propionamide, and isobutyramide. These enzyme inducing agents are more effective when added sequentially during the cultivation of bacteria at a concentration ordinarily of lower than 15 g/liter, preferably of 10 g/liter or lower. The pH of the culture medium is of the order of 6 to 9, preferably of the order of 7 to 8, while the cultivation temperature is of the order of 20° to 37° C., preferably of the order of 25° to 30° C., and the cultivation time is about 1 to 3 days.

EXPERIMENTAL EXAMPLES

In the following experimental examples, 1 ml of a culture fluid was added to 9 ml of a phosphate buffer solution (pH 7.5) containing 2.8% by weight of acrylonitrile, and the resulting solution was caused to react at 10° C. for 10 to 60 minutes. The quantity of acrylamide obtained was measured by means of gas chromatography, and the hydratase activity of the bacteria exhibited in the hydration of acrylonitrile was determined on the basis of the data thus obtained, the capability of producing 1 μmole of acrylamide per ml of a culture fluid per minute being designated as 1 unit.

EXAMPLE 1

To five separate but identical lots of a culture medium, each comprising 10 g/liter of sucrose, 2 g/liter of $K_2HPO_4$, 0.5 g/liter of $MgSO_4.7H_2O$, 1 g/liter of NaCl, and 10 mg/liter of $FeSO_4.7H_2O$ was added L-cysteine at respectively different concentrations ranging from 0.1 to 5.0 g/liter. The pH of each culture medium was adjusted to 7.2, and 100 ml of each resulting culture medium was sterilized in a 500-ml Erlenmeyer flask.

After cooling, 0.4 g of isobutyronitrile was added to each sterilized culture medium which was then inoculated with 0.5 ml of a culture fluid obtained by precultivating *Pseudomonas chlororaphis,* strain B 23 (FERM BP-187), in a culture medium of the above composition containing no L-cysteine, and shaking cultivation was carried out aerobically at 25° C. for 2 days.

For comparison purposes, cultivation was carried out similarly without addition of L-cysteine.

The cell concentration of each of the culture fluids and the nitrile hydratase activity thereof exhibited in the hydration of acrylonitrile were measured. The results obtained are shown in Table 2.

TABLE 2

| Quantity of L-Cysteine Added (g/liter) | Cell Concentration (g/liter) | Nitrile Hydratase Activity (unit) |
|---|---|---|
| 0 Comparison Example | 1.39 | 20.3 |
| 0.1 | 1.37 | 27.1 |
| 0.5 | 1.40 | 33.3 |
| 1.0 | 1.50 | 42.2 |
| 2.0 | 1.80 | 56.3 |
| 5.0 | 1.79 | 39.9 |

EXAMPLE 2

To three separate but identical lots of a culture medium, each comprising 10 g/liter of sucrose, 2 g/liter of $K_2HPO_4$, 0.5 g/liter of $MgSO_4.7H_2O$, 1 g/liter of NaCl, and 10 mg/liter of $FeSO_4.7H_2O$ were added D-cysteine, D,L-cysteine, and L-cystine respectively in three instances at a concentration of 1.0 g/liter. The pH of each culture medium was adjusted to 7.2, and 100 ml of each resulting culture medium was sterilized in a 500-ml Erlenmeyer flask.

After cooling, 0.4 g of isobutyronitrile was added to each sterilized culture medium which was then inoculated with 0.5 ml of a culture fluid obtained by precultivating *Pseudomonas chlororaphis,* strain B 23 (FERM BP-187), in a culture medium of the above composition containing no cysteine or cystine, and shaking cultivation was carried out aerobically at 25° C. for 2 days.

For comparison purposes, cultivation was carried out similarly without addition of cysteine or cystine.

The cell concentration of each of the culture fluids and the nitrile hydratase activity thereof exhibited in the hydration of acrylonitrile were measured. The results obtained are set forth in Table 3.

TABLE 3

| Species of Additive | Quantity (g/liter) | Cell Concentration (g/liter) | Nitrile Hydratase Activity (unit) |
|---|---|---|---|
| No additive (Comparison Example) | 0 | 1.41 | 21.2 |
| D-Cysteine | 1.0 | 1.39 | 34.0 |
| D.L-Cysteine | 1.0 | 1.40 | 40.7 |
| L-Cystine | 1.0 | 1.45 | 38.3 |

EXAMPLE 3

To two separate but identical lots of a culture medium, each comprising 10 g/liter of glycerol, 2 g/liter of $K_2HPO_4$, 0.5 g/liter of $MgSO_4.7H_2O$, 1 g/liter of NaCl, and 10 mg/liter of $FeSO_4.7H_2O$ were added L-cysteine and L-cystine, respectively, in two instances at a concentration of 1.0 g/liter. The pH of each culture medium was adjusted to 7.2, and 100 ml of each resulting culture medium was sterilized in a 500-ml Erlenmeyer flask.

After cooling, 0.8 g of propionitrile was added to each sterilized culture medium, which was then inoculated with 0.5 ml of a culture fluid obtained by precultivating Pseudomonas sp., strain PS 1 (FERM BP-188), in a culture medium of the above composition containing no cysteine or cystine, and shaking cultivation was carried out aerobically at 25° C. for 2 days.

For comparison purposes, cultivation was carried out under similar conditions except that neither cysteine nor cystine was added.

The cell concentration of each of the culture fluids and the nitrile hydratase activity thereof exhibited in the hydration of acrylonitrile were measured. The results obtained were as shown in Table 4.

TABLE 4

| Species of Additive | Quantity (g/liter) | Cell Concentration (g/liter) | Nitrile Hydratase Activity (unit) |
|---|---|---|---|
| No additive (Comparison Example) | 0 | 3.21 | 15.8 |
| L-Cysteine | 1.0 | 3.38 | 30.5 |
| L-Cystine | 1.0 | 3.31 | 27.6 |

EXAMPLE 4

To two separate but identical lots of a culture medium, each comprising 10 g/liter of sucrose, 2 g/liter of $K_2HPO_4$, 0.5 g/liter of $MgSO_4.7H_2O$, 1 g/liter of NaCl, 10 mg/liter of $FeSO_4.7H_2O$, and 2 g/liter of yeast extract was added L-cysteine at a concentration of 1 and 2 g/liter, respectively. The pH of each culture medium was adjusted to 7.2, and 100 ml of each resultant culture medium was sterilized in a 500-ml Erlenmeyer flask.

After cooling, 0.4 g of isobutyronitrile was added to each sterilized culture medium, which was then inoculated with 0.5 ml of a culture fluid obtained by precultivating *Pseudomonas chlororaphis*, strain B 23 (FERM BP-187), in a culture medium of the above composition containing no L-cysteine, and cultivation was carried out under aerobic conditions at 25° C. for 2 days.

For comparison purposes, cultivation was carried out similarly without addition of L-cysteine. The cell concentration of each of the culture fluids and nitrile hydratase activity thereof were measured, whereupon the results shown in Table 5 were obtained.

TABLE 5

| Quantity of L-Cysteine Added (g/liter) | Cell Concentration (g/liter) | Nitrile Hydratase Activity (unit) |
|---|---|---|
| 0 (Comparison Example) | 3.32 | 36.5 |
| 1.0 | 3.53 | 73.1 |
| 2.0 | 4.05 | 105.7 |

What is claimed is:

1. A method for increasing the nitrile hydratase activity of Pseudomonas bacteria which comprises providing a biologically pure culture of Pseudomonas bacteria capable of producing nitrile hydratase, adding an enzyme inducing agent and an enzymatic activity improving agent selected from cysteine, cystine and a combination thereof in an amount effective to increase the nitrile hydratase activity of the Pseudomonas bacteria to a culture medium for the Pseudomonas bacteria and cultivating the Pseudomonas bacteria in the presence of the enzyme inducing agent and enzymatic activity improving agent.

2. The method as claimed in claim 1, wherein the concentration of the enzymatic activity improving agent in the culture medium is in the range of from 0.1 to 5.0 g/liter.

3. The method as claimed in claim 1, wherein the Pseudomonas bacteria capable of producing nitrile hydratase is *Pseudomonas chlororaphis*, strain B 23 (FERM BP-187), or Pseudomonas sp., strain PS 1 (FERM BP-188).

4. The method as claimed in claim 1 in which the pH of the culture medium is of the order of 6 to 9.

5. The method as claimed in claim 1 in which the enzyme inducing agent is selected from a member of the group consisting of propionitrile, isobutyronitrile, propionamide and isobutyramide.

* * * * *